(12) United States Patent
Ford

(10) Patent No.: US 8,550,251 B1
(45) Date of Patent: Oct. 8, 2013

(54) DIABETIC TWO-FOLD MEDICAL CASE

(76) Inventor: Edna Ford, Morrow, GA (US)

(*) Notice: Subject to any disclaimer, the term of this patent is extended or adjusted under 35 U.S.C. 154(b) by 0 days.

(21) Appl. No.: 13/465,006

(22) Filed: May 6, 2012

(51) Int. Cl.
*B65D 69/00* (2006.01)

(52) U.S. Cl.
USPC .......................................... 206/570; 206/370

(58) Field of Classification Search
USPC ................. 206/570, 571, 576, 577, 229, 233, 206/363, 370, 438; 220/4.28, 23.83, 23.9, 220/503, 523, 527, 528, 500, 4.01
See application file for complete search history.

(56) References Cited

U.S. PATENT DOCUMENTS

| | | | | |
|---|---|---|---|---|
| 941,608 | A | * | 11/1909 | Benson .......................... 312/209 |
| 1,042,249 | A | * | 10/1912 | Mickelson ................... 62/457.7 |
| 1,374,849 | A | * | 4/1921 | Greene ......................... 206/581 |
| 1,481,194 | A | * | 1/1924 | Fischer ......................... 220/503 |
| 1,944,502 | A | * | 1/1934 | Factor ............................. 190/33 |
| 2,988,125 | A | * | 6/1961 | Reynolds .................. 206/316.2 |
| 3,558,205 | A | * | 1/1971 | Mueller ........................ 312/209 |
| 4,250,998 | A | | 2/1981 | Taylor |
| 4,303,158 | A | * | 12/1981 | Perkins ......................... 206/373 |
| 4,429,793 | A | | 2/1984 | Ehmann |
| 4,446,970 | A | | 5/1984 | Further |
| 4,768,651 | A | * | 9/1988 | Lanius ..................... 206/315.11 |
| 5,114,007 | A | * | 5/1992 | Chen ............................ 206/373 |
| 5,390,791 | A | | 2/1995 | Yeager |
| 5,826,719 | A | * | 10/1998 | Chen ............................ 206/373 |
| 6,959,814 | B1 | | 11/2005 | Hyman |
| 8,286,794 | B1 | * | 10/2012 | Agadzi ......................... 206/570 |
| 2005/0236296 | A1 | | 10/2005 | Horkins et al. |
| 2007/0007164 | A1 | | 1/2007 | Lord |
| 2007/0265511 | A1 | | 11/2007 | Renouf |
| 2008/0283426 | A1 | | 11/2008 | Primer et al. |
| 2009/0152159 | A1 | | 6/2009 | Beeman |

* cited by examiner

*Primary Examiner* — Jacob K Ackun
*Assistant Examiner* — Jenine Pagan
(74) *Attorney, Agent, or Firm* — J.T. Hollin, Attorney at Law, P.C.

(57) ABSTRACT

Disclosed is a combination medical case including multiple storage compartments, specifically for use by a diabetic patient. The medical case comprises a base compartment sized and shaped to contain a plurality of storage cubicles for the containment of prescription medicine bottles. The base compartment further contains a means for attachment of a planar-shaped equipment tray which may hold a glucose meter and a quantity of syringes or other supplies. A removable drawer, having a hinged top, rests on parallel supporting ledges integral to the inner walls of the base compartment. A shelf is sized and shaped to horizontally fit atop the removable drawer, within the confines of the base compartment. Receptacles within either the base compartment or the drawer may contain a pharmaceutical formulation comprising insulin. The medical case allows the patient to access needed medical and nutritional supplies and access equipment necessary to monitor and/or control his/her glucose level.

2 Claims, 5 Drawing Sheets

DIABETIC TWO-FOLD MEDICAL CASE

REFERENCE TO RELATED APPLICATION

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

BACKGROUND OF THE INVENTION (1) Field of the Invention

There has always been a need for effective and rapid treatment of diabetic patients during times when they are distant from their primary care giver or an appropriate medical facility. Over the years there has developed a variety of means of provision of an adequately stocked portable kit that may be used to treat unexpected medical emergencies or accidents at the location where such incidents occur. The inventive concept presented herein generally is concerned with an apparatus and method for enabling a diabetic patient or the patient's caregiver to instantly access needed medical supplies, equipment, or a supply of insulin, particularly when engaged in travel.

A diabetic person may often be inconvenienced by the need to readily organize and/or access a variety of instruments necessary for maintaining his/her health. Therefore, it is desirable to provide a medical kit and storage case that is convenient for patients and their caregivers. It is further desirable to provide a kit that provides a user with all implements and supplies useful or necessary in caring for problems specific to diabetes. The inventive concept disclosed provides a unique solution to these requirements.

(2) Description of the Related Art

US patent application publication #2009/0152159 (Jun. 18, 2009) while not a medical kit per se, does disclose a self-contained portable kit that provides the convenience and ability to easily carry various necessary items that bring comfort to the user of the kit. The kit contains a closable, folding wallet having a plurality of sealable containers and a pricking device removably fastened to an inner surface of the wallet for storing a variety of items or substances. A closable pocket is coupled to another inner surface of the wallet for storing a variety of items.

The inventor in US patent application publication #2008/0283426 (Nov. 20, 2008) designed a medical treatment package including at least one medical care product and an individual container in which the product(s) is stored prior to usage. The medical treatment package further includes a booklet-type label affixed to an exterior surface of at least one individual container, the booklet-type label including on its interior surface medical treatment information.

US patent application publication #2007/0265511 (Nov. 15, 2007) is an invention comprising a diabetes blood glucose test site cleaning kit having a container housing a multiplicity of swabs moistened with an aqueous cleansing solution wherein the swabs are layered within the container to facilitate one by one removal. The container is dimensioned such that the cleaning kit readily fits into a blood glucose meter wallet.

US patent application publication 2007/0007164 A1 (Jan. 11, 2007) discloses an apparatus for storing and dispensing health care items which comprises a container having multiple compartments. At least some of the compartments contain health care items and are labeled with indicia relating to the health care item contained therein.

US patent application publication 2005/0236296 A1 (Oct. 27, 2005) presents a carry case provided for use by a diabetic patient. The carry case comprises a first compartment sized and shaped to contain an aerosolization apparatus, a second compartment sized and shaped to contain one or more receptacles for use in the aerosolization apparatus, and a third compartment sized and shaped to contain a glucose meter. One receptacle may contain an aerosolizable pharmaceutical formulation comprising insulin.

U.S. Pat. No. 6,959,814 B1 (Nov. 1, 2005) A portable insulin and accessory kit for diabetics that is a case made of polymeric or waterproof material having an inside portion divided in three equal sections, each section securing and storing insulin and accessories such as an insulin pen or syringe, alcohol cloths, or similar accessories for sterilization and a supply of additional needles. The kit is foldable and provides hook and loop fasteners for a secure closure. In addition, an insulin storage box with is provided having a hingedly attached cover attached to a bottom portion having divided sections for the storage of various items.

The inventor in U.S. Pat. No. 5,390,791 (Feb. 21, 1995) designed a portable medicine carrier and protector for storing and transporting medicine stored in vials, comprising a thin-walled medicine carrier. The carrier is substantially filled with a paraffinic hydrocarbon, an alpha olefin or a material such as dimethyl sulfoxide. A cavity is disposed in a top surface of the carrier formed from a plurality of different semicircular compartments. Each of the compartments has a different cross-sectional radius, thereby allowing medicine vials of differing sizes. A plurality of solid-ribbed members is disposed transversely in the cavity, so as to prevent direct contact between the carrier and the medicine vials.

U.S. Pat. No. 4,446,970 (May 8, 1984) The invention herein is a diabetic set in the form of a pressure resistant case for containing at least one insulin bottle, a syringe and, optionally, a supply of alcohol cloths or similar accessories for sterilization. The case includes a container and a lid that telescopically encloses the container in the manner of a cap. The container includes means for securing the insulin bottle and syringe as to facilitate hygienic administration of insulin under all conditions.

U.S. Pat. No. 4,429,793 (Feb. 7, 1984) presents a diabetic traveling case compact enough to be pocket-sized. The pocket-sized case is equipped to carry at least one bottle of insulin, as well as a refrigerant which maintains the insulin at a suitably low temperature to avoid spoiling.

In U.S. Pat. No. 4,250,998 (Feb. 17, 1981) a diabetic travel kit is formed by an insulated container having a cavity in which is received a cooling medium container having an annular cooling medium chamber surrounding a top opening compartment. An insulated lid closes the cavity.

BRIEF SUMMARY OF THE INVENTIVE CONCEPT

The inventive concept herein discloses a medical case comprising multi-compartmented storage sections especially designed for use by a diabetic patient. The medical case comprises a main base compartment sized and shaped to contain a plurality of storage cubicles for the containment of prescription medicine bottles. The base compartment further contains a means for vertical attachment of a planar-shaped equipment tray to an interior wall of the base compartment. The equipment tray may hold a glucose meter and a quantity of syringes or other supplies. A removable storage tray rests horizontally on parallel support ledges integral to the inner walls of the base compartment. A smaller removable drawer, having a hinged top, is sized and shaped to slidingly fit within the confines of the base compartment. Receptacles within either the base compartment or sliding drawer may contain pharmaceutical formulations comprising insulin or other necessary medication. The base compartment further comprises a lengthwise hinged lid which may be handedly closed and latched when the sliding drawer is fully positioned within the base compartment. In its preferred embodiment, the medical case allows a diabetic patient to access needed medical and nutritional supplies and also monitor and control his/her glucose level.

DETAILED DESCRIPTION OF THE INVENTIVE CONCEPT

The objects, features, and advantages of the concept presented in this application are more readily understood when referring to the accompanying drawings. The drawings, totaling five figures, show the basic functions of various embodiments and methods. In the several figures, like reference numbers are used in each figure to correspond to the same component as may be depicted in other figures.

The present inventive concept is designed to be a portable equipment, supply, medication, and accessory case for diabetic patients. The device may be constructed of plastic, fiberglass, metal, composite materials, or other suitable material. There is a variety of inside compartments and integral containers conveniently useable for securing and storing insulin and medical necessities. The medical case 1 comprising the present invention 1 provides a compact, efficient, and sanitary means for travel.

Figure 1:
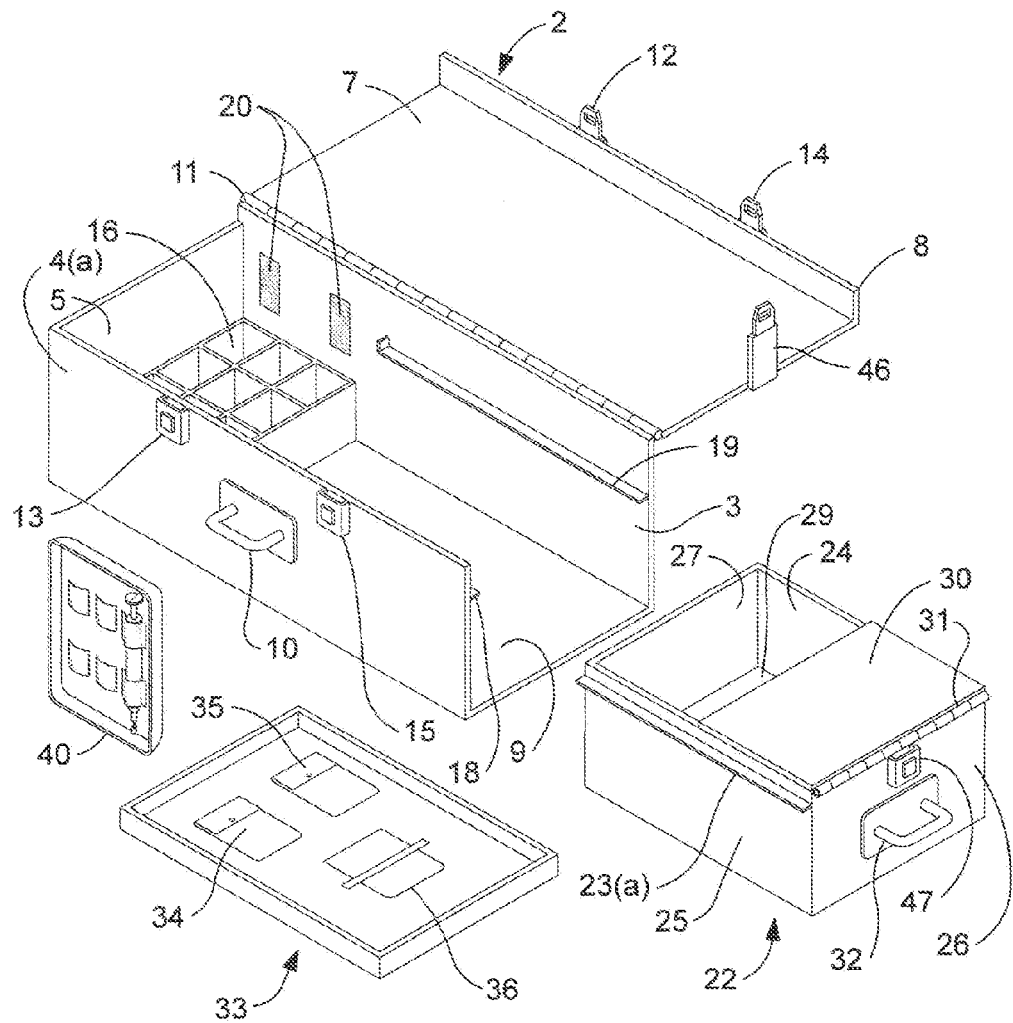
FIG. 1 illustrates an exploded view of the portable medical case, showing the base compartment, the drawer, shelf and tray.
Figure 2:
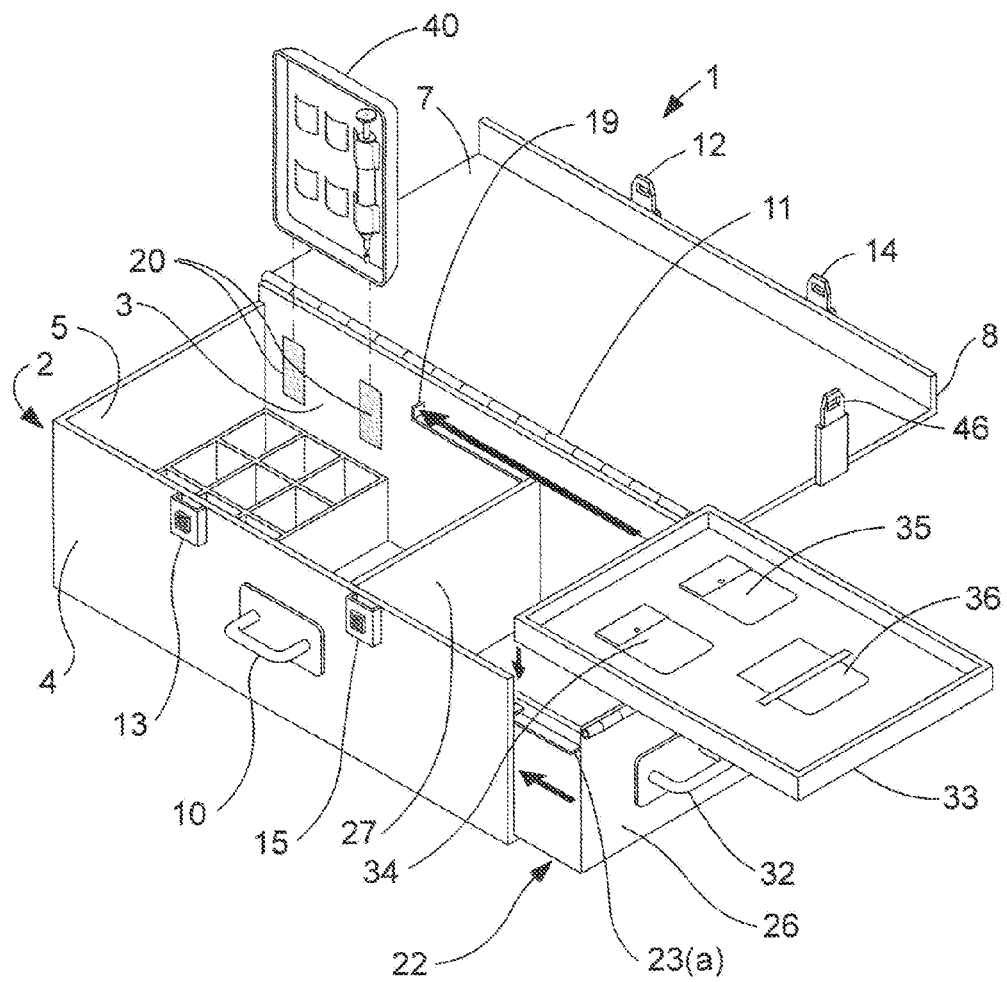
FIG. 2 depicts the portable medical case with the drawer partially inserted, the shelf proximate its position in the device, and the tray slightly above its normal retained location.

In viewing FIG. 1, there is presented an exploded presentation of the twofold medical case 1. It can be seen that the main component of the present medical case 1 comprises a base compartment 2 (the base) that is essentially a rectangular boxlike structure with five interior surfaces. The five interior surfaces comprise a base floor 9, an elongated base front wall 4 [the exterior base front wall 4(a) is shown in FIG. 1], a base end wall 5, an elongated base back wall 3, and the interior surface of a hinged base top 7. The elongated base back wall 3 of the preferred embodiment further comprises a hinged connector 11 which provides for the attachment of the base top 7 to the top of the base back wall 3 as shown in FIG. 1 and FIG. 2.

The base back wall 3 shows an integral back ledge 19 (the front ledge 18 is out of view) which provides horizontal support for a removable drawer 22. The removable drawer 22 slidingly fits onto the front and back ledges 18, 19 by means of a front flange 23(a) and back flange 23(b) both of which are attached to the exterior of the drawer front wall 25 and the exterior of the drawer back wall 24. Once the drawer 22 is positioned fully within the base compartment 2 a shelf 33 is horizontally placed atop the removable drawer 22. An accessory tray 40 is vertically attached to the interior surface of the base back wall 3. The base top 7 is thereafter closed and latched upon the entire assemblage.

Figure 3:
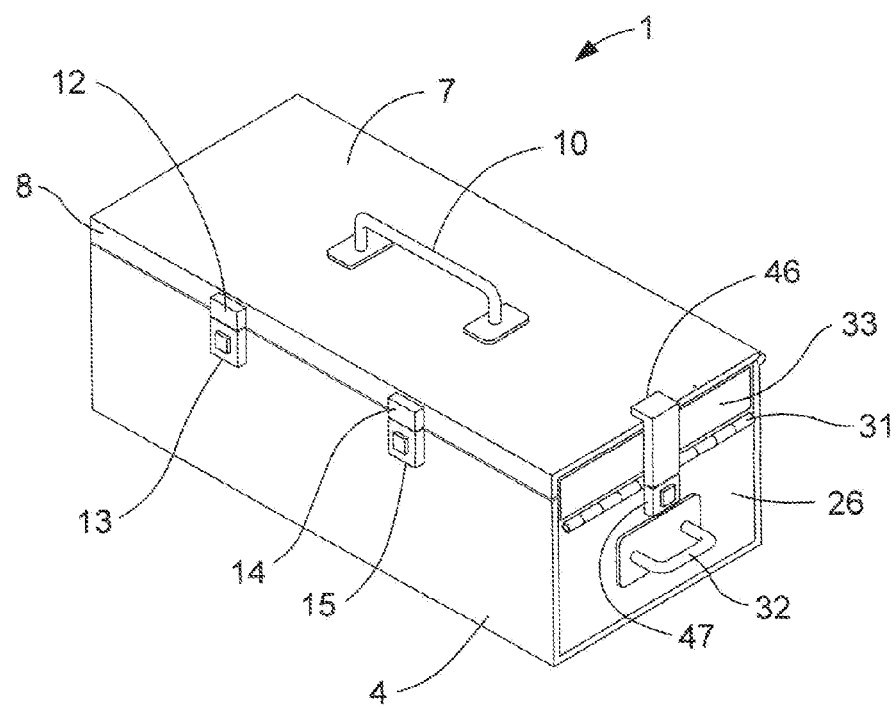
FIG. 3 presents the medical case in its fully closed configuration, with its three latches closed.

The base top 7 is constructed with a base lid 8 oriented lengthwise and perpendicularly to the front edge of the base top 7. The base back wall 3 comprises a slightly higher vertical dimension in comparison with the base closed end 5 and the base front wall 4, so as to provide allowance for the depth of the base lid 8 in the act of closure of the medical case 1. The base compartment 2 further contains a plurality of cubicles 16 integral to the compartment base floor 9. The cubicles 16 may be used for storage of a number of medical vials or similar containers, items of nourishment, or other necessary supplies. In FIG. 3, there is shown a carry handle 10 attached to the exterior surface of the base top 7.

In the preferred embodiment, two latching mechanisms, oriented with reference to the base lid 8, comprise a left latch tongue 12, a left latch clasp 13, a right latch tongue 14, and a right latch clasp, 15 provide a secure means for closing the medical case 1 when required. Further, an end latch tongue 46 and an end latch clasp 47, when conjoined, are used to provide additional security during times when the drawer 22 is fully closed within the confines of the base compartment 2.

Again referring to FIG. 1, there is also shown removable drawer 22, a vertically-attached tray 40, a storage shelf 33, and the storage cubicles 16. The removable drawer 22 further comprises a hinged flap 30, a handle 32, a latch clasp 47, a front flange 23(a), and a back flange 23(b) [out of view]. The two flanges 23(a), 23(b) are constructed so as to allow the drawer 22 to be slidably positioned within the base compartment 2 when a user simultaneously positions the two flanges 23(a) and 23(b) upon the front ledge 18 and back ledge 19, respectively, of the base compartment 2. When necessary, the drawer flap 30 may be opened to load or unload items while the drawer 22 is only partially extended from the interior of the base compartment 2.

In FIG. 1, there is further shown a storage shelf 33 to which are secured three storage packets 34, 35, and 36. The storage packets 34, 35, and 36, in the preferred embodiment, are normally used for the storage of extra needles for the diabetic patient. The storage shelf 33 comprises dimensions which allow for it to be placed atop the removable drawer 22 prior to closing the medical case.

FIG. 2 displays the removable drawer 22 in the process of being inserted into the compartment base 2. The removable drawer 22 may be inserted in the direction of the arrow until the outer surface of the drawer right end 26 becomes flush with the edge of the base front wall 4. A front flange 23(a) and a corresponding back flange 23(b) (not in view) both integral to the removable drawer 22, are simultaneously placed atop the horizontal front ledge 18 and back ledge 19, both interiorly fabricated within the drawer 22. The removable drawer 22 is thereupon easily slid along the ledges 18, 19 into position within the base compartment 2. Once the removable drawer 22 is in place, the shelf 33 is placed atop the removable drawer 22.

FIG. 2 further displays the tray 40 and the vertical orientation in which the tray 40 will be stored within the base compartment 2. FIG. 2 also shows two hook components 20 of a hook-and-felt fastening mechanism attached to the interior surface of the base back wall 3. Two correspondingly-placed felt components of a hook-and-felt mechanism are permanently attached to the back side of the tray 40 so as to facilitate the fastening of the tray 40 to the interior surface of the base back wall 3. The tray 40 may also be attached to the interior surface of the base back wall 3 by other appropriate fastening means.

Turning to FIG. 3, shown therein is a perspective view of the fully closed medical case 1. The storage shelf 33 has been placed atop the removable drawer 22 such that one end of the storage shelf 33 is flush with the removable drawer right end 26. Both right and left latch tongues 12, 14, permanently fixed upon the lid 8 of the medical case 1, facilitate closure of the medical case 1 by insertion into right and left latch clasps 13, 15, which are integral to the base compartment 2 front wall 4. Further, when the medical case 1 is closed, an end latch tongue 46, integral to the medical case 1 top 7, makes inserting contact with an end latch clasp 47 fabricated onto the removable drawer right end 26. The medical case 1 is thereupon fully closed and secured and a user may then transport the medical case 1 by use of the carry handle 10 fixed to the top 7 of the medical case 1.

Figure 4:
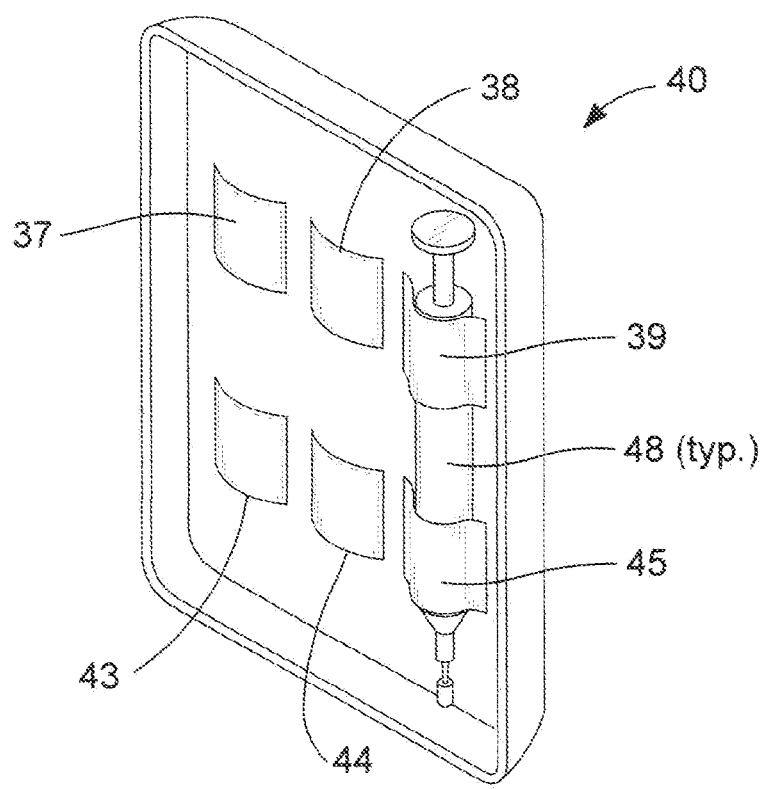
FIG. 4 is an illustration of tray component of the medical case, with a typical medical syringe shown supported within two retainer straps.

FIG. 4 is a view of the tray 40 as used in this inventive concept. The tray 40 has provisions for the containment of up to three syringes. A typical syringe 48 is shown secured between an elastic upper retainer strap 39 and a lower retainer strap 45. Two other paired retainer straps 37-43, and 38-44 may also be used for securing syringes. On the unseen opposite side of the tray 40, there are two felt components of a hook-and-felt fastening mechanism, sized and located to correspond with the two hook components of the hook-and-felt fastening mechanism affixed to the interior surface of the base back wall 3 of the medical case 1. The tray 40 may also be secured in place with other fastening means, including, but not limited to, snaps, magnets, latches, slots, and other suitable means.

Figure 5:
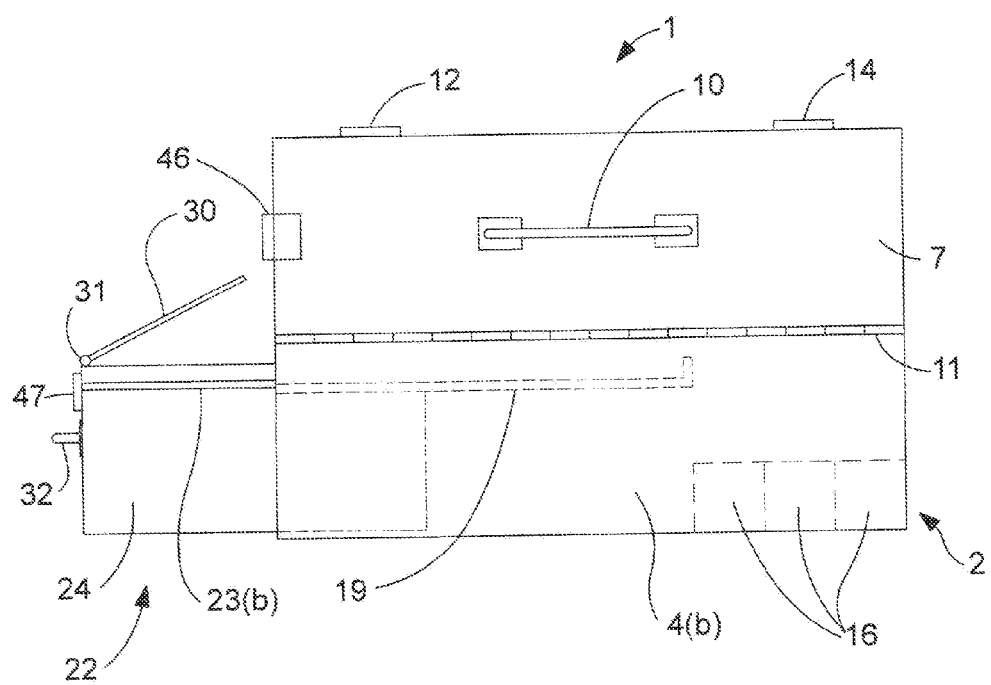
FIG. 5 shows a view of the rear of the medical case with the base compartment top open and the removable drawer partially inserted into the base compartment.

FIG. 5 presents a view of the rear of the medical case 1 showing the base back wall 4(*b*) and the top 7 fully open by means of the hinge 11 connection. The removable drawer 22 is partially inserted as indicated by dashed lines indicating the back ledge 19 which provides rear support for the back flange 23(*b*) of the drawer 22.

While preferred embodiments of the present inventive concept have been shown and disclosed herein, it will be obvious to those persons skilled in the art that such embodiments are presented by way of example only and not as a limitation to the scope of the inventive concept. Numerous variations, changes, and substitutions may occur or be suggested to those skilled in the art without departing from the intent, scope, and totality of the inventive concept. Such variations, changes, and substitutions may involve other features which are already known per se and which may be used instead of, or in addition to features already disclosed herein. Accordingly, it is intended that this inventive concept not be limited by the scope of the accompanying claims.

What is claimed is:

1. A multi-purpose medical case comprising a base compartment, a removable drawer, a shelf and a tray, wherein
    (a) said base compartment comprises a front wall, a back wall, a closed end, an open end, a floor, a closeable base top, said base top having a lengthwise orthogonal base lid; a plurality of cubicles individually affixed to the floor; a front ledge attached to the interior of said front wall and parallel to said floor; a back ledge attached to the interior of said back wall and parallel to said floor; and a means for securely closing said base lid to the top of said front wall;
    (b) said removable drawer further comprises a front wall, a back wall, a left end, a right end, and a bottom; a drawer flap hingedly attached to the top of the right end of said drawer; an end latch clasp attached to the upper center of said right end, a handle centeredly attached to the exterior of said right end, a front flange attached lengthwise to the exterior of said front wall; end; a back flange attached lengthwise to the exterior of said back wall;
    (c) said shelf further comprises an essentially planar structure having dimensions compatible with the floor dimensions of said removable drawer, and a plurality of closeable packets attached to the upper surface of said shelf; and
    (d) said tray comprises a primarily planar structure having three pairs of longitudinally-aligned, flexible restraining straps, whereby
        upon closing of the medical case, said removable drawer fits onto the floor of said base compartment, said shelf is horizontally placed atop the removable drawer, said tray is vertically attached to an interior surface wall of said base compartment, and the top and lid of the base compartment being thereafter closed upon the entire assemblage.

2. A multi-purpose medical case comprising a base compartment, a removable drawer, a shelf and a tray further comprising:
    (a) a base compartment comprising a front wall, a back wall, a closed end, an open end, a floor, a hingedly closeable base top; a plurality of cubicles abutting each other and affixed to the floor; a front ledge attached to the interior of said front wall and parallel to said floor; a back ledge attached to the interior of said back wall and parallel to said floor; a base lid orthogonally attached lengthwise to said base top, said base lid further having two spaced latched tongues attached to the edge of said base lid; an end latch tongue orthogonally attached to the upper right end of said base top; two spaced latch clasps attached to front wall at a distance coinciding with said spaced latch tongues;
    (b) a removable drawer comprising a front wall, a back wall, a left end, a right end, and a bottom; a drawer flap hingedly attached to the top of said right end; an end latch clasp attached to the upper center of said right end, a handle centeredly attached to the exterior of said right end, a front flange attached lengthwise to the exterior of said front wall; end; a back flange attached lengthwise to the exterior of said back wall;
    (c) a shelf comprising an essentially planar structure having dimensions compatible with the floor dimensions of said removable drawer, and a plurality of closeable packets attached to the upper surface of said shelf; and
    (d) a tray comprising a primarily planar structure having three pairs of longitudinally-aligned, flexible restraining straps, whereby
    said removable drawer slidingly fits onto the front and back ledges of said base compartment, said shelf is horizontally placed atop the removable drawer, and said tray is vertically attached to an interior surface wall of said base compartment, the top of the base compartment being thereafter latched closed upon the entire assemblage by means of said corresponding latch tongues and latch clasps.

* * * * *